(12) United States Patent
Yang et al.

(10) Patent No.: US 8,101,342 B2
(45) Date of Patent: Jan. 24, 2012

(54) DNA VACCINE FOR TREATING OR PREVENTING CERVICAL CANCER COMPRISING A GENE ENCODING HPV PROTEIN

(75) Inventors: Joo Sung Yang, Seoul (KR); Sang Woo Kim, Euiwang-si (KR); Jung Ah Choi, Suwon-si (KR)

(73) Assignee: Sungkyunkwan University Foundation For Corporate Collaboration, Gyeonggi-do (KR)

( * ) Notice: Subject to any disclaimer, the term of this patent is extended or adjusted under 35 U.S.C. 154(b) by 253 days.

(21) Appl. No.: 11/995,624

(22) PCT Filed: Aug. 28, 2007

(86) PCT No.: PCT/KR2007/004140
§ 371 (c)(1),
(2), (4) Date: Mar. 16, 2009

(87) PCT Pub. No.: WO2008/026869
PCT Pub. Date: Mar. 6, 2008

(65) Prior Publication Data
US 2010/0285058 A1    Nov. 11, 2010

(30) Foreign Application Priority Data
Aug. 28, 2006  (KR) .................. 10-2006-0081645

(51) Int. Cl.
*C12Q 1/70*  (2006.01)
(52) U.S. Cl. .......................... 435/5; 435/91.1
(58) Field of Classification Search .............. None
See application file for complete search history.

(56) References Cited

U.S. PATENT DOCUMENTS

| | | | | |
|---|---|---|---|---|
| 6,007,806 A | * | 12/1999 | Lathe et al. ............ | 424/93.2 |
| 6,123,948 A | * | 9/2000 | Whittle et al. .......... | 424/204.1 |
| 6,290,965 B1 | * | 9/2001 | Jansen et al. ............ | 424/199.1 |
| 6,726,912 B1 | * | 4/2004 | Webb et al. ............. | 424/199.1 |
| 7,482,015 B2 | * | 1/2009 | Bryan et al. ............ | 424/204.1 |
| 7,482,428 B2 | * | 1/2009 | Jansen et al. ........... | 530/300 |
| 2005/0118139 A1 | * | 6/2005 | Huang et al. ............ | 424/93.2 |
| 2008/0260765 A1 | * | 10/2008 | Wu et al. ................ | 424/186.1 |

FOREIGN PATENT DOCUMENTS

| | | |
|---|---|---|
| WO | WO 02/38769 A2 | 5/2002 |
| WO | WO 03/018055 A1 | 3/2003 |
| WO | WO 03/077942 A2 | 9/2003 |

OTHER PUBLICATIONS

Disbrow et al (Journal of Virology, May 2005, vol. 79, No. 9, pp. 5839-5846).*
Disbrow, et al., "Codon Optimization of the HPV-16 E5 Gene Enhances Protein Expression", Virology, 311, 2003, pp. 105-114.
Extended European Search Report dated Dec. 4, 2009 for corresponding European Application No. 07793734.0-2401.
International Search Report dated Dec. 5, 2007 for corresponding International Application No. PCT/KR2007/004140.
Liu et al.; "*Induction of CD8 T Cells by Vaccination with Recombinant Adenovirus Expressing Human Papillomavirus Type 16 E5 Gene Reduces Tumor Growth*"; Journal of Virology; Oct. 2000; pp. 9083-9089.
Tsai et al.; "*The Biochemical and Biological Functions of Human Papillomavirus Type 16 E5 Protein*"; Archives of Virology; Jun. 2, 2003; pp. 1445-1453.

* cited by examiner

*Primary Examiner* — Ali R. Salimi
(74) *Attorney, Agent, or Firm* — Casimir Jones, S.C.

(57) ABSTRACT

Disclosed herein is a DNA vaccine for treating cervical cancer including an E5 gene of human papillomavirus (HPV). Also, disclosed is a combination DNA vaccine for preventing and treating cervical cancer including a gene encoding HPV L1 and/or L2 along with the HPV E5 gene.

9 Claims, 13 Drawing Sheets

[Figure 1]
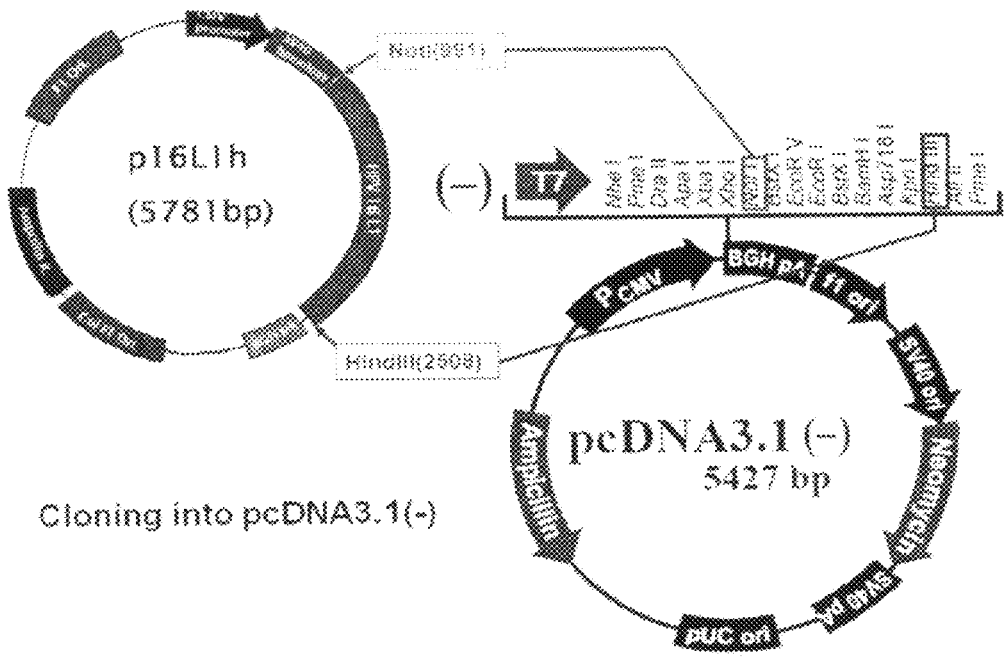
[Figure 2]
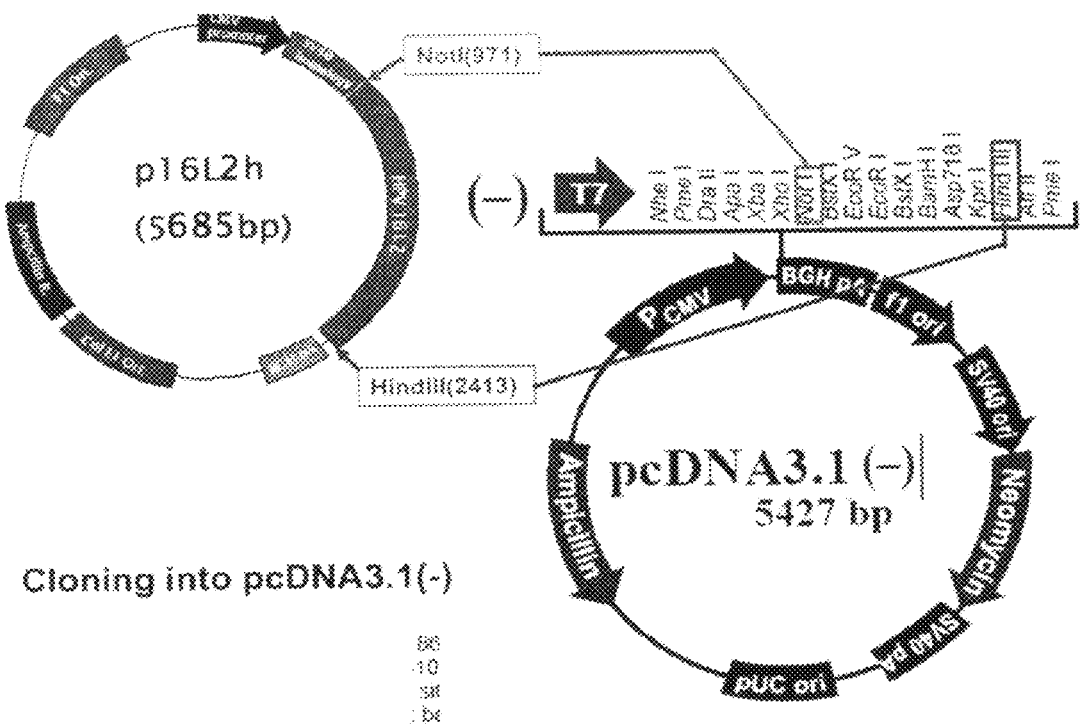

[Figure 3]
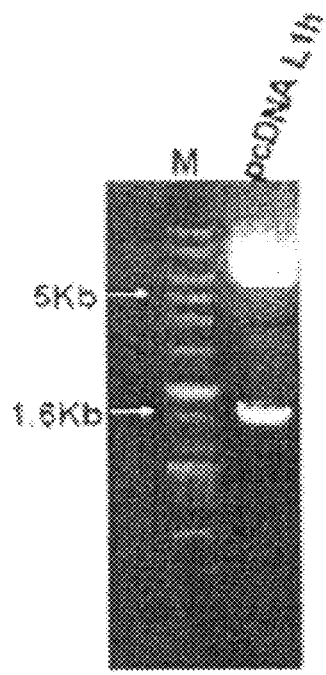
[Figure 4]
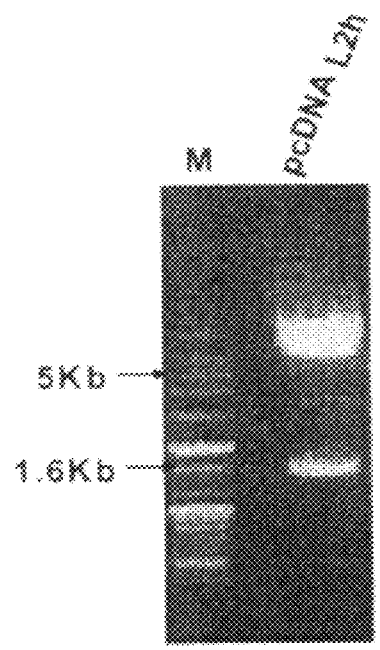

HPV18 E5 sense primer (Sequence No.11)

5'-GCGGCC AAGCTT GCCGCC ATG ATGXCAAATCTGGAIACTG -3'
      HindIII    KOZAK

HPV18 E5 anti-sense primer (Sequence No.12)

5'-ATC GCC CTCGAG TTAIGIAATCAGAAACCGTGC -3'
          XhoI

[Figure 8]

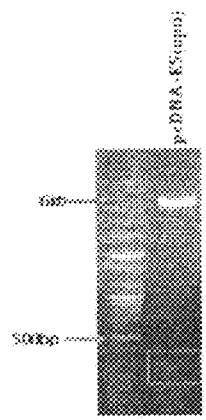

[Figure 9]

E5 Opti align result

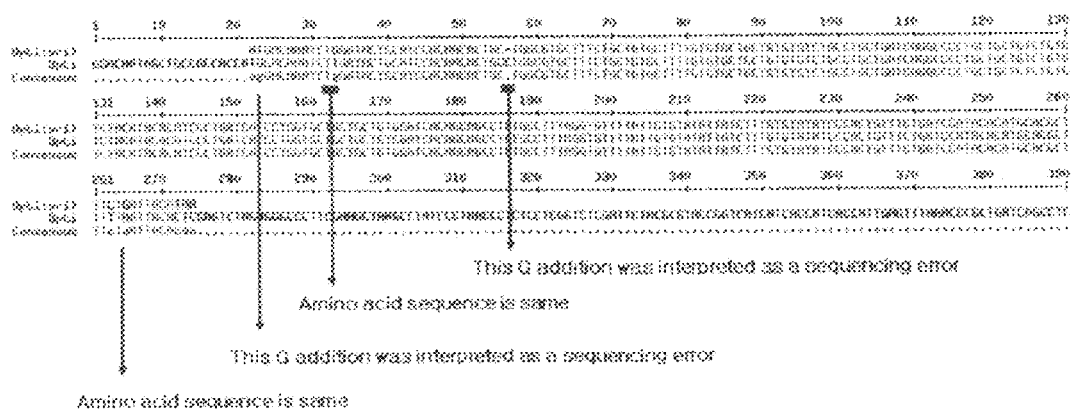

This G addition was interpreted as a sequencing error

Amino acid sequence is same

This G addition was interpreted as a sequencing error

Amino acid sequence is same

[Figure 10]
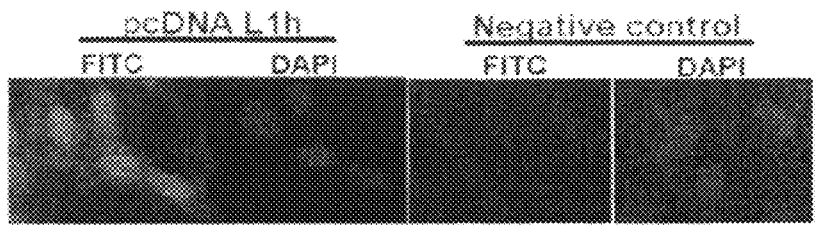
[Figure 11]
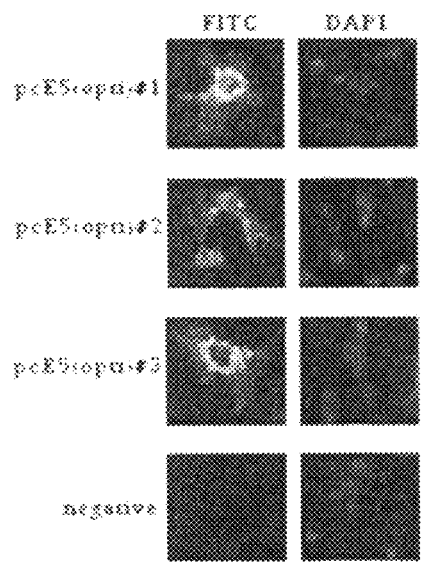
[Figure 12]
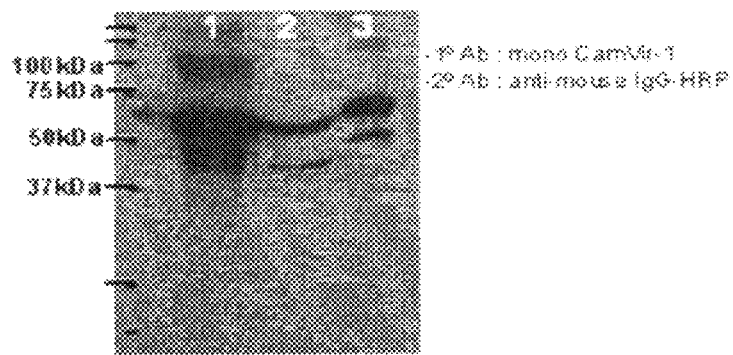

[Figure 13]
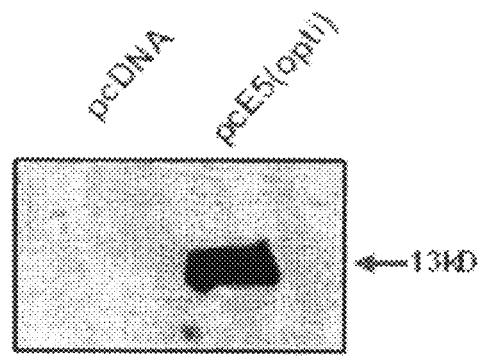
[Figure 14]
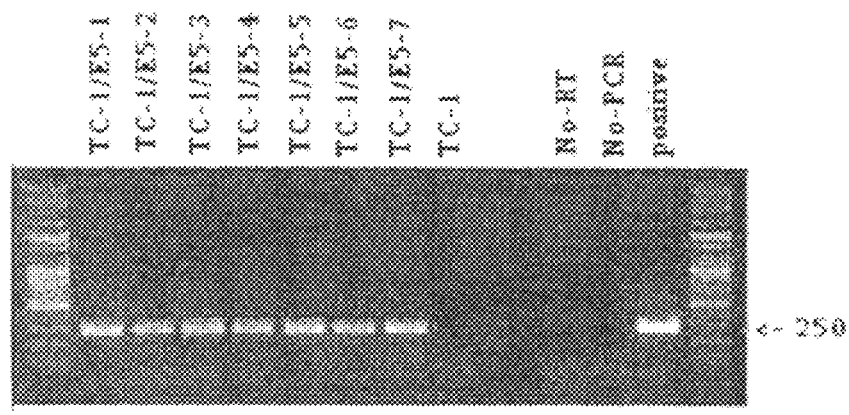
[Figure 15]
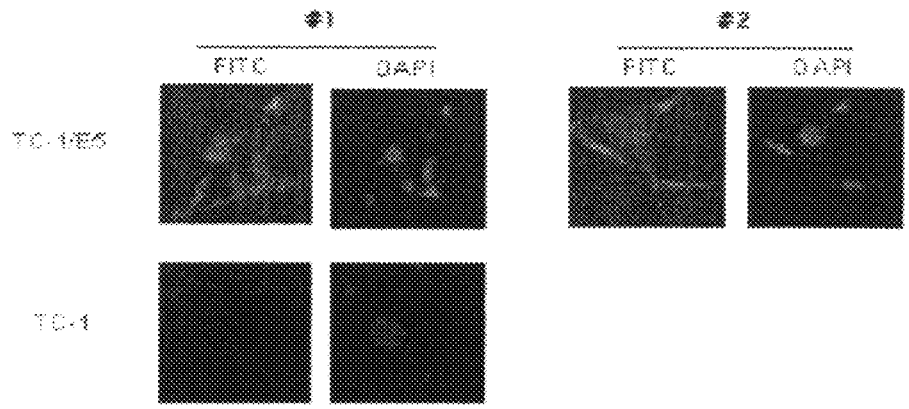

[Figure 16]
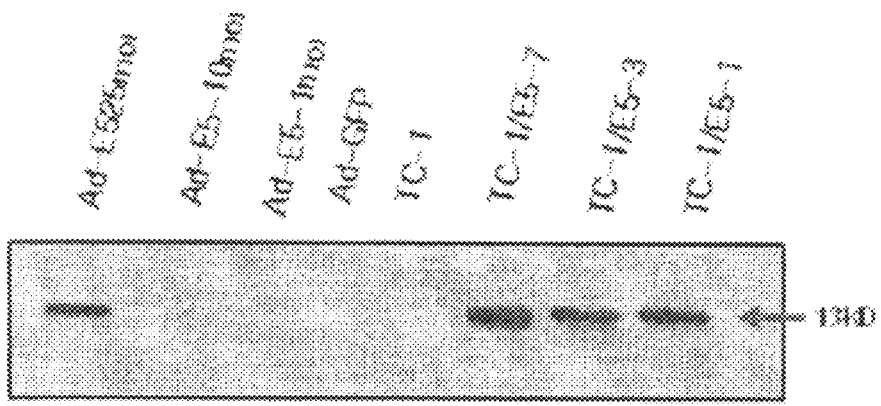
[Figure 17]
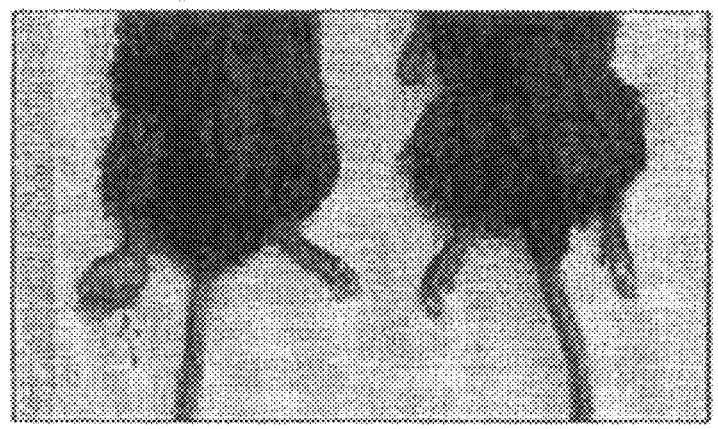
[Figure 18]
Tumor tissue from TC-1/E5 tumor cell challenged mouse
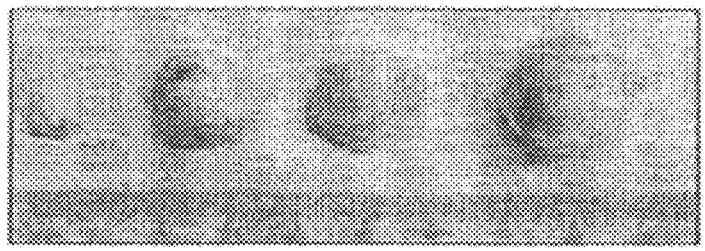

[Figure 19]

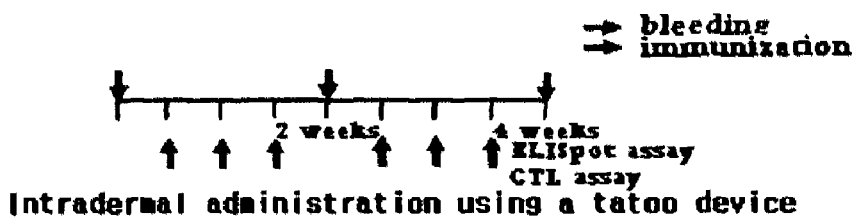

Intradermal administration using a tatoo device

Mouse group

| | immunization |
|---|---|
| Group 1(6) | pcL1h + pcE5(opti) |
| Group 2(6) | pcL1h + pcE5(opti)+pcIL15 |
| Group 3(6) | pcL1h + pcE5(opti)+pcM-CSF |
| Group 4(6) | PBS |

[Figure 20]

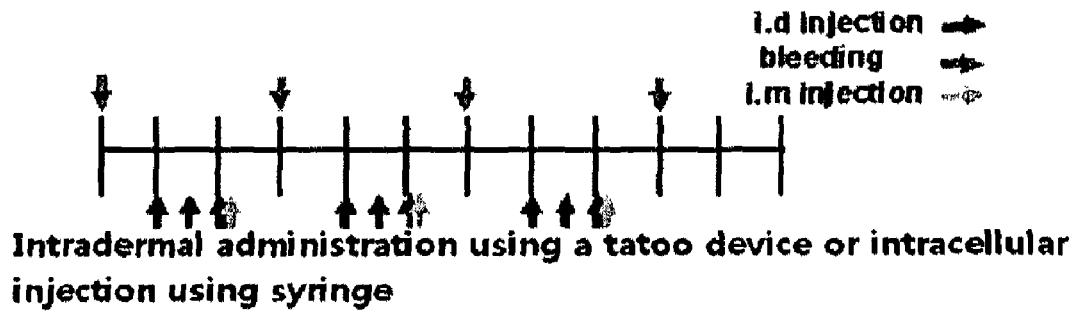

Intradermal administration using a tatoo device or intracellular injection using syringe

| | Immunization |
|---|---|
| Group1 | pcL1h+pcE5+LTB(intradermal) |
| Group2 | pcL1h+pcE5(intradermal) |
| Group3 | pcL1h+pcE5+LTB(intramuscular) |
| Group4 | pcL1h+pcE5(intramuscular) |
| Group5 | pcDNA(intradermal) |
| Group6 | pcDNA(intramuscular) |

[Figure 21]
|  | Immunization |
|---|---|
| Group1 | pcL1h+pcL2h DNA (Intradermal) |
| Group2 | pcL1h+pcL2h DNA (Intramuscular) |
| Group3 | pcE5 DNA (Intradermal) |
| Group4 | pcE5 DNA (intramuscular) |
| Group5 | pcL1h+pcE5 DNA (Intradermal) |
| Group6 | pcL1h+pcE5 DNA (Intramuscular) |
| Group7 | pcL1h+pcL2h+pcE5 DNA (Intradermal) |
| Group8 | pcL1h+pcL2h+pcE5 DNA (Intramuscular) |
| Group9 | pcDNA (Intradermal) |
| Group10 | pcDNA (Intramuscular) |
[Figure 22]
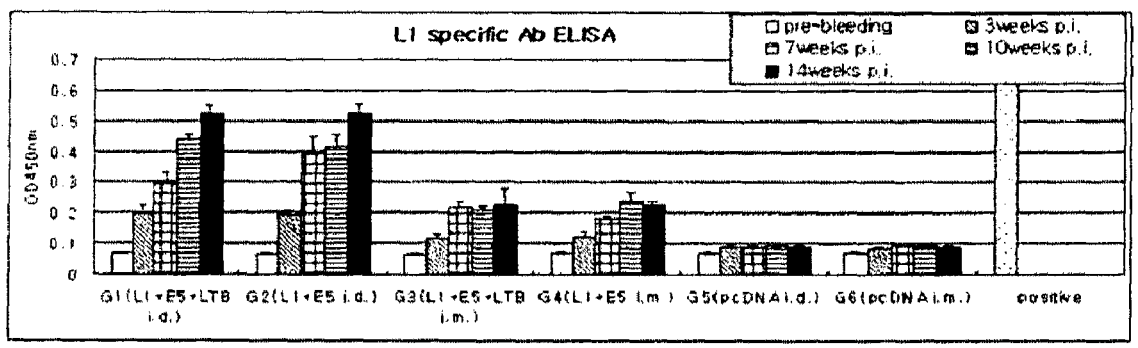
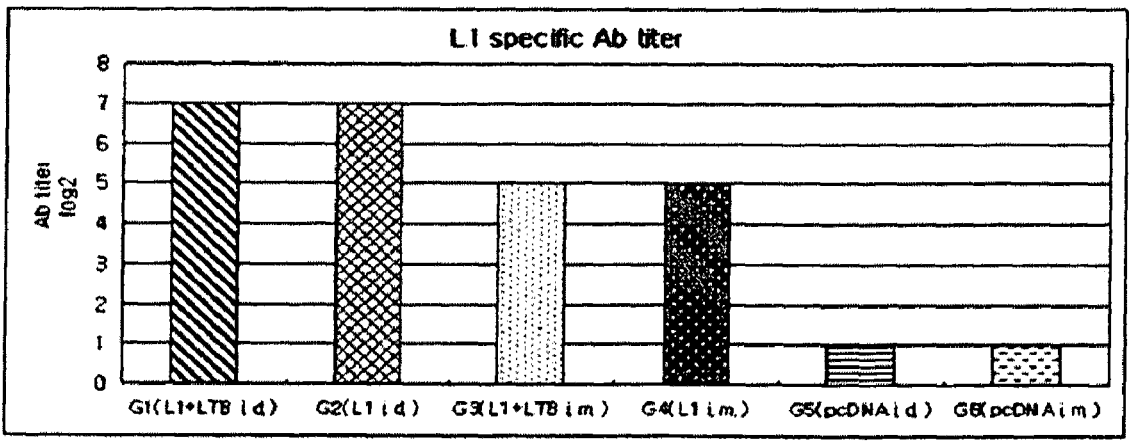

[Figure 23]
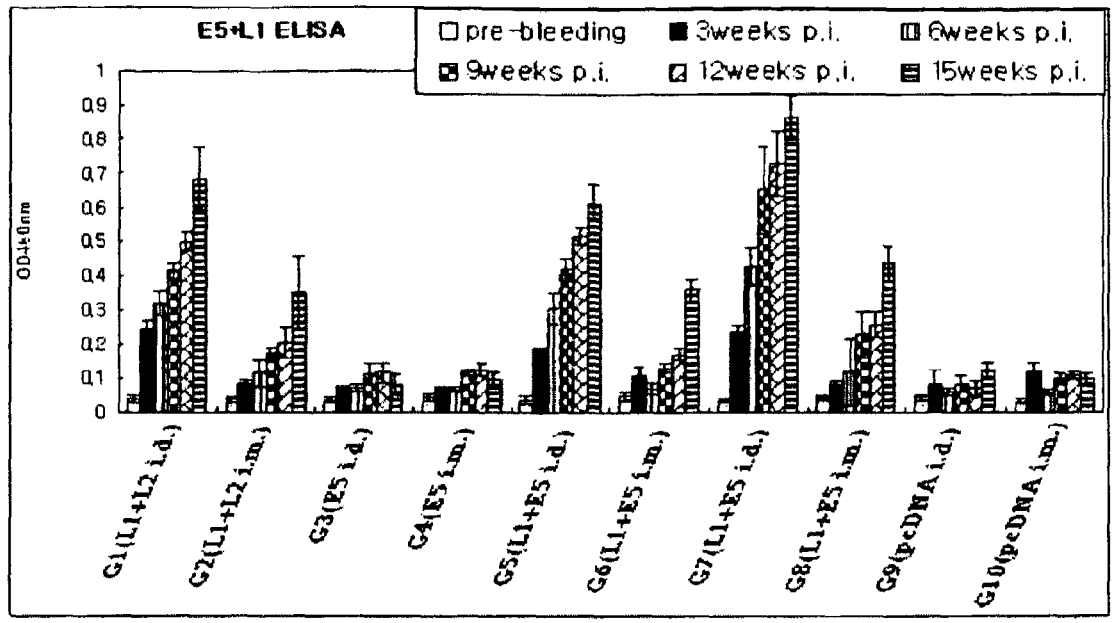
[Figure 24]
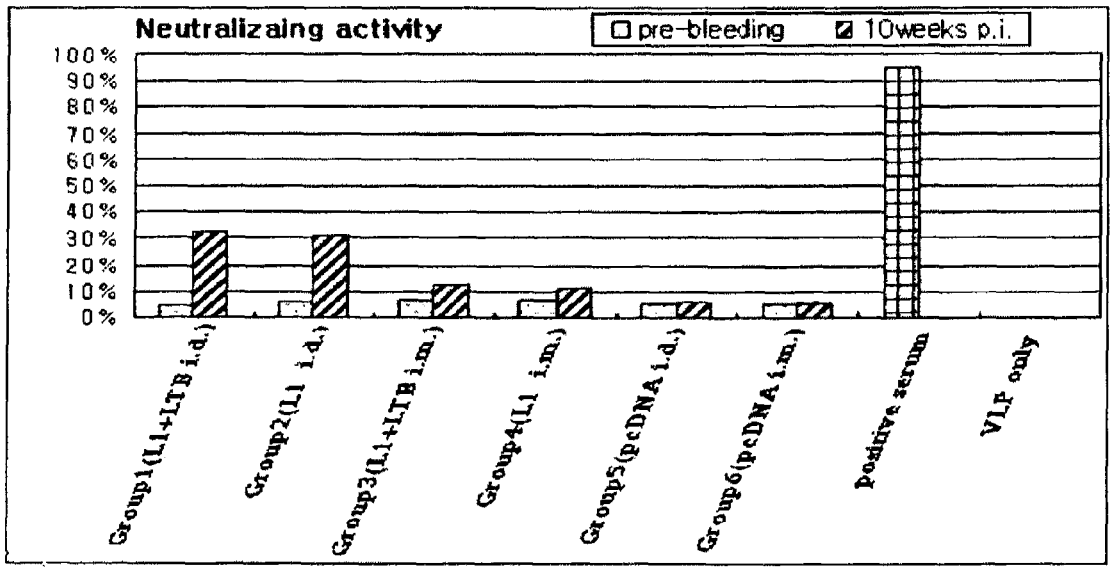

[Figure 25]
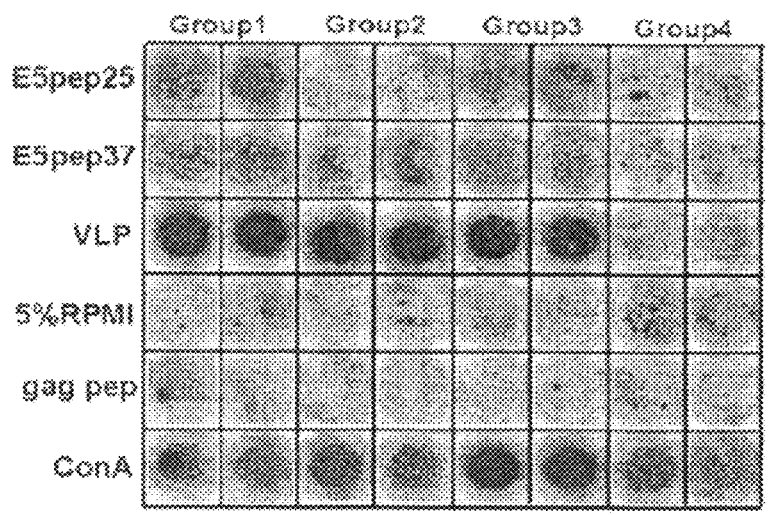
[Figure 26]
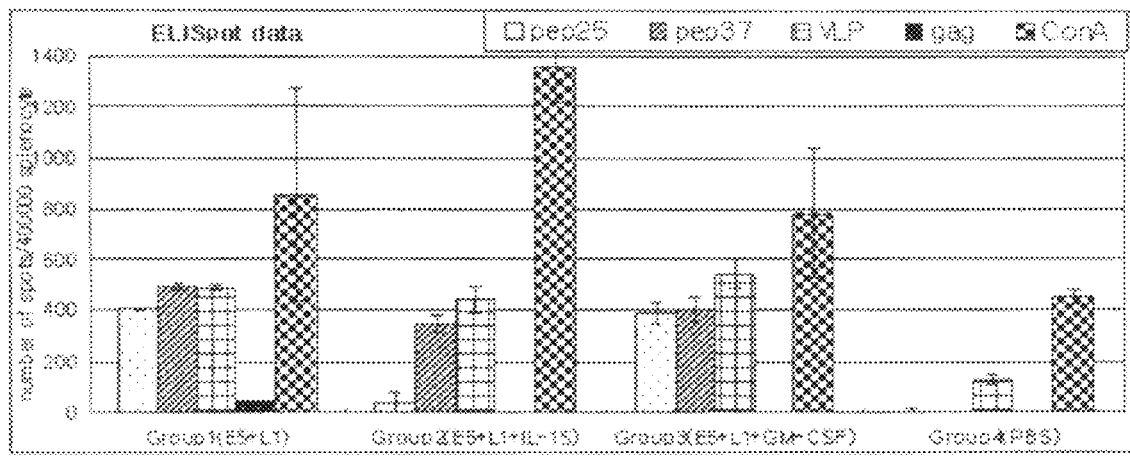

[Figure 27]
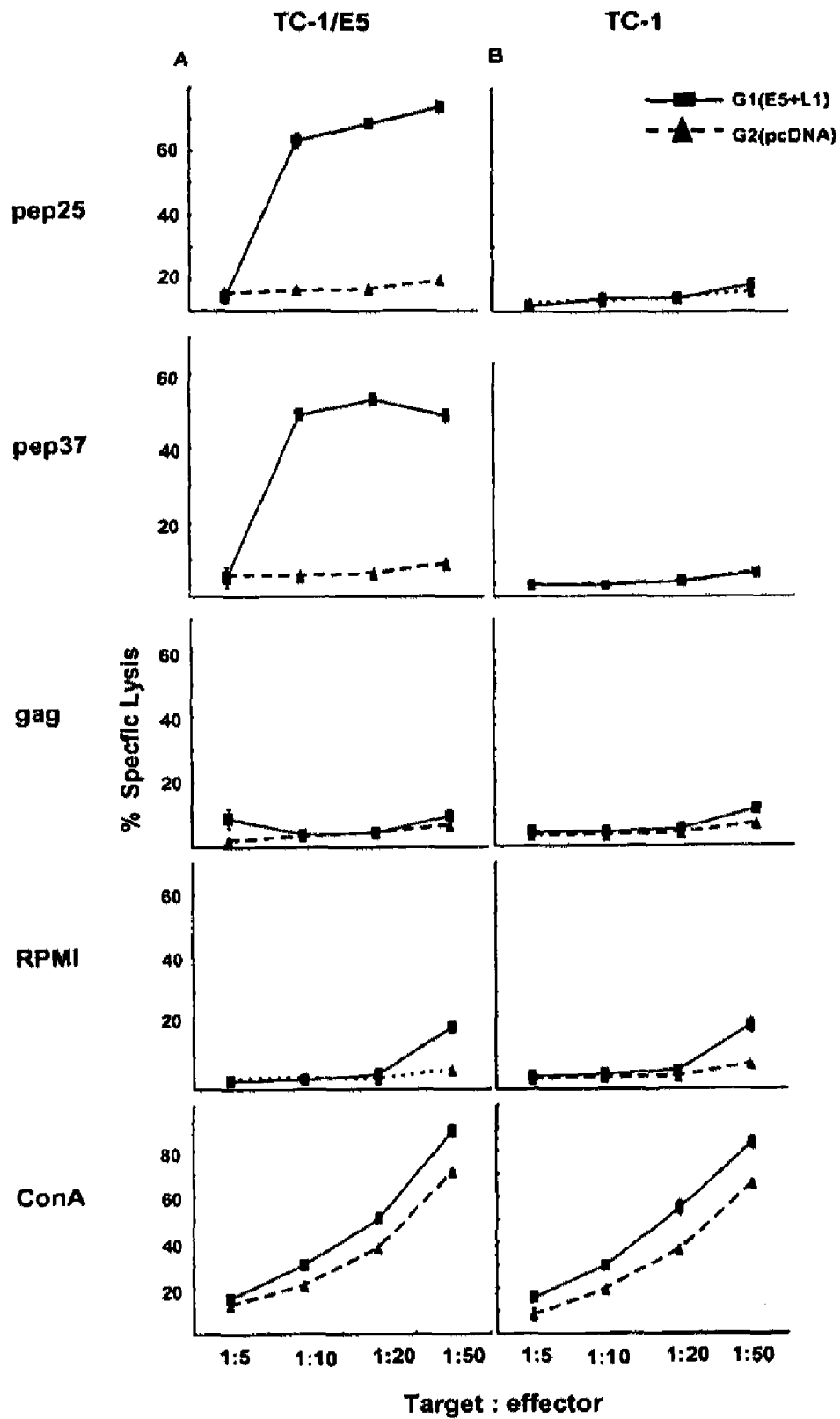

[Figure 28]
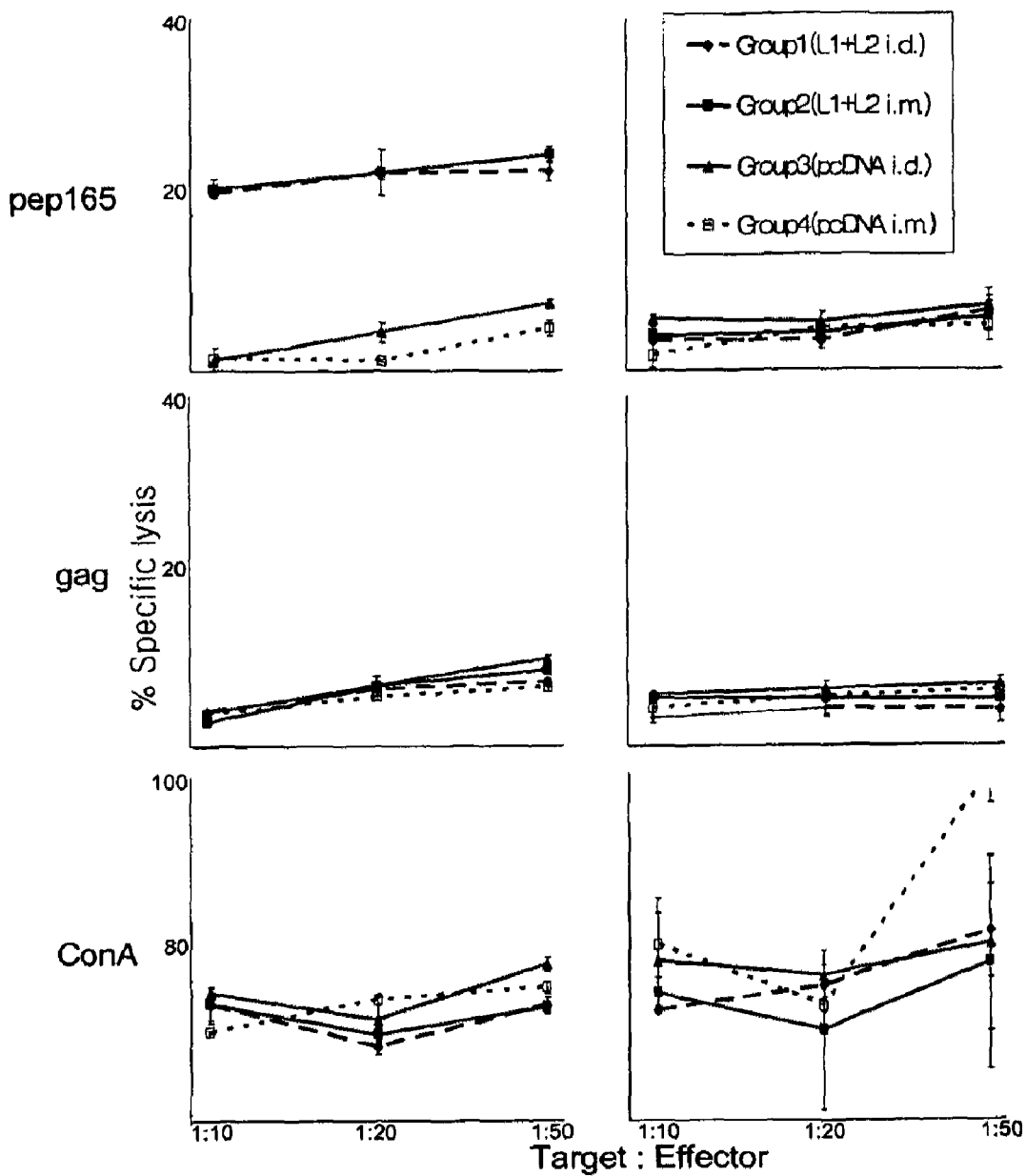

DNA VACCINE FOR TREATING OR PREVENTING CERVICAL CANCER COMPRISING A GENE ENCODING HPV PROTEIN

TECHNICAL FIELD

The present invention relates to a DNA vaccine for preventing and treating cervical cancer, and more particularly, to a combination DNA vaccine using the capsid L1 gene and the E5 gene of human papillomavirus, which is found in all cases of cervical cancer.

BACKGROUND ART

Human papillomavirus (HPV) has a circular double-stranded genome that is about kbp in length. The genome of all HPV types contains open reading frames (ORFs), which are DNA regions coding for proteins having similar properties, and is divided into two major regions: early (E) and late (L) regions. The early region of about 4.5 kbp codes for genes which are associated with functions including viral DNA replication (E1), induction or suppression of the action of DNA encoding a protein inducing malignant transformation of host cells (E2), the synthesis of proteins responsible for the growth of host cells and viruses (E4), stimulation of the activity of epidermal growth factor (EGF) and colony stimulator factor (CSF) receptors (E5), and malignant transformation through the permanent survival of cells, activation of oncogenes, and inactivation of tumor suppressor genes (E7). In particular, the oncogenic E6 and E7 proteins, which are expressed after HPV infects the epithelial cells of a host, bind to the tumor suppressor proteins of host cells, p53 and pRB, respectively, and thus inhibit the function of the tumor suppressor proteins, resulting in the neoplastic transformation of infected cells.

The late region of 2.5 kbp comprises genes coding for viral major (L1) and minor (L2) capsid proteins and a non-coding region 1 kbp long, which is called the long control region (LCR), and regulates the transcription and translation of the two late genes.

With recent rapid advances in molecular biological techniques, the genetic structure of HPV has been identified, and thus, the genomic sequences of many HPV genotypes were revealed. HPV is classified according to the difference in DNA sequences of E6, E7 and L1 ORFs. When the nucleotide sequences of the ORFs differ by more than 10%, an HPV is assigned a new genotype. HPV subtypes differ by 2% to 10%, and HPV variants differ by less than 2%. To date, over 120 types of HPV have been identified according to the classification.

HPV has been associated with anogenital cancer, laryngeal cancer and tongue cancer. HPV has also been considered a necessary factor for the development and persistence of cervical cancer. Cervical cancer, a malignant tumor that occurs in tissues of the cervix, accounts for more than 95% of all uterine cancers. Worldwide, cervical cancer is the second most common cancer in women after breast cancer, and about 44,000 new cases are reported each year.

Certain types of HPV are classified as "high-risk" because they have high potential for progression to cancer, including cervical cancer. High-risk HPV types include 16, 18, 26, 30, 31, 34, 35, 39, 45, 51, 52, 53, 56, 58, 59, 61, 66, 67, 68, 69, 70, and 73. Other types, such as HPV 2, 3, 6, 7, 10, 13, 32, 40, 42, 43, 44, 55, 54 and 57, are categorized as "low-risk" because they have lower potential for malignancy.

Due to the close relationship between HPV infection and cervical cancer development and the high death rates of cervical cancer, various strategies have been designed to develop effective vaccines against HPV for the prevention and treatment of cervical cancer.

Prophylactic vaccines, which are given before exposure to HPV, induce the generation of virus neutralizing antibodies, and thus prevent mucosal HPV infection. Therapeutic vaccines induce a cell-mediated immune response targeted against epithelial cells from persons infected with HPV. Therapeutic vaccines eliminate cells expressing the late genes when administered upon viral replication, and, when administered upon the integration of viral DNA into a host cell genome, target E6 and E7 oncoproteins and thus control or suppress the growth of existing HPV-associated tumors. Thus, prophylactic vaccines should be administered prior to HPV infection, while therapeutic vaccines should be administered when lesions are generated by infection or HPV. With respect to action targets according to the molecular biological mechanism of HPV infection, prophylactic vaccines target the capsid L1 or L2 proteins and induce neutralizing antibodies thereto, while most therapeutic vaccines are intended to stimulate the immune system against E6 or E7 early antigens.

Prophylactic vaccines are disadvantageous in that the use of prophylactic vaccines alone cannot treat HPV that has infected cells in the basal layer and has already transformed cells. Prophylactic vaccines induce antigen-antibody responses, but established infections cannot be treated via humoral immunity, but can be treated only via cellular immunity. The therapeutic limitation of prophylacticvaccines has driven the development of therapeutic vaccines. Most therapeutic vaccines target the viral E6 and E7 proteins, which are consistently retained and expressed in cells of the basal layer and cells that have already transformed.

Since premalignant lesions usually contain fewer tumor cells than invasive malignancy, immune responses induced in early lesions may eradicate tumor cells more effectively. In addition, after the early tumorigenesis' stage, MHC class I and II are expressed at lower levels, which could hamper the presentation of tumor antigens, leading to decreased immune responses. Some studies have reported that the lymphocyte proliferation responses to HPV-16 E5 are inversely proportional to the severity of the squamous intraepithelial neoplasia lesions (SILs). Hence, in E5-expressed precancerous lesions, such as SILs and condyloma, using E5 as a vaccine target to induce cytotoxic T cell (CTL) activity specific to E5, which is expressed in earlier stages of HPV infection, may be a good strategy to prevent premalignant lesions from progressing into invasive cervical cancers.

In addition, the L1 major capsid protein, which is produced during the late stage of HPV infection and assembles the replicated HPV genomic DNA into infectious virions in terminally differentiated epithelial cells, has been repotted to induce effectively humoral and cellular immune responses. Hence, the use of the E5 gene along with the L1 gene offers effective treatment effects by inducing L1-specific cellular immunity during all stages of viral infection.

In this regard, the present inventors intended to develop a therapeutic HPV vaccine that targets E5 and effectively eradicates tumors in earlier stages. Also, the present inventors intended to develop a combination DNA vaccine having prophylactic effects as well as therapeutic effects during all stages of viral infection by adding, to the above vaccine, a gene encoding an L1 and/or L2 capsid protein of HPV. As a result, a DNA vaccine comprising both an HPV E5 gene and an HPV L1 and/or an L2 gene was found to induce effectively humoral and cellular immune responses. In addition, when the vaccine was injected intradermally using a tattoo device, it showed remarkably increased immune responses even with very low amounts of antigens and in a short period of time, thereby leading to the present invention.

DISCLOSURE

Technical Problem

It is therefore an object of the present invention to provide a DNA vaccine for treating cervical cancer comprising an HPV E5 gene.

It is another object of the present invention to provide a combination DNA vaccine for preventing and treating cervical cancer comprising a gene encoding HPV capsid L1 and/or L2 along with the HPV E5 gene.

It is a further object of the present invention to provide a vaccine composition comprising the vaccine and a pharmaceutically acceptable carrier.

It is yet another object of the present invention to provide a method of injecting the vaccine intradermally to enhance the immune efficiency of the vaccine, and a vaccine composition suitable for intradermal administration.

DESCRIPTION OF DRAWINGS

The above and other objects, features and advantages of the present invention will be more clearly understood from the following detailed description taken in conjunction with the accompanying drawings, in which:

FIG. 1 schematically shows the process of cloning an L1h gene of HPV into an expression vector;

FIG. 2 schematically shows the process of cloning an L2h gene of HPV into an expression vector;

FIG. 3 shows the band patterns of an HPV L1h gene-cloned vector after restriction endonuclease digestion and gel electrophoresis;

FIG. 4 shows the band patterns of an HPV L2h gene-cloned vector after restriction endonuclease digestion and gel electrophoresis;

FIG. 5 is a nucleotide sequence alignment in which the nucleotide sequence of the L1h gene, carried in pcDNA-L1h, is compared with that of original p16L1h FIG. 6 is a nucleotide sequence alignment in which the nucleotide sequence of the L2h gene, carried in pcDNA-L2h, is compared with that of original p16L2h FIG. 7 shows PCR primers specific to a codon-optimized HPV E5 gene;

FIG. 8 shows the band patterns of a HPV E5 gene-cloned vector (pcDNA-E5) after restriction endonuclease digestion and gel electrophoresis;

FIG. 9 is a nucleotide sequence alignment in which the nucleotide sequence of the codon-optimized E5 gene, carried in pcDNA-E5, is compared with that of an original HPV E5 gene;

FIG. 10 shows the results of an indirect immunofluorescence assay (IFA) on pcDNA-L1h-transfected cells and a negative control;

FIG. 11 shows the results of IFA on pcDNA-E5-transfected cells and a negative control;

FIG. 12 shows the results of Western blotting for the expression of pcDNA-L1h plasmid (lane 1: lysate of cells transfected with p16L1h plasmid; lane 2: lysate of cells transfected with pcDNA-L1h lane 3: virus-like particle (VLP), which is the L1 protein purified using Opti-Prep);

FIG. 13 shows the results of Western blotting for lysate of cells transfected with pcDNA-E5

FIG. 14 shows the results of RT-PCR for E5 gene expression in a TC-1/E5 cell line;

FIG. 15 shows the results of IFA on the TC-1/E5 cell line;

FIG. 16 shows the results of Western blotting using the TC-1/E5 cell line;

FIG. 17 is a photograph showing tumor formation when the TC-1/E5 cell line was injected subcutaneously into the hind legs of C57BL/6 mice;

FIG. 18 is a photograph showing tumor tissues isolated from mice in which tumors were formed;

FIG. 19 illustrates three in vivo immunization experiment schedules using pcL1h and pcE5, wherein the pcL1h and pcE5 plasmids were administered to the mice in each group using a tattoo device, Group 2 was administered with pcL1h and pcE5 plus pcIL-15, Group 3 with pcL1h and pcE5 plus pcGM-CSF, and Group 4, as a negative control, with PBS only;

FIG. 20 shows the immunization schedule for the comparison of immunization effects between intradermal administration using a tattoo device and intramuscular injection (Group 1 and Group 2: administered with pcL1h and pcE5 plasmids using a tattoo device, and Group 1 was further administered with LTB; Group 3 and Group 4: administered intramuscularly with the same plasmids as Groups 1 and 2, plus LTB for Group 3 only; Group 5 and Group 6 (negative controls): administered intradermally and intramuscularly, respectively, with pcDNA, an empty plasmid not containing any HPV gene);

FIG. 21 shows another immunization schedule (Group 1 and Group 2: administered intradermally and intramuscularly, respectively, with a combination of pcL1h and pcL2h Group 3 Group 4: administered intradermally and intramuscularly, respectively, with pcE5 alone; Group 5: administered intradermally with pcL1h and pcE5 Group 6: administered intramuscularly with pcL1h and pcE5 Group 7: administered intradermally with pcL1 h, pcL2h and pcE5 Group 8: administered intramuscularly with pcL1h, pcL2h and pcE5 Group 9 and Group 10 (negative controls): administered intradermally and intramuscularly, respectively, with pcDNA alone);

FIG. 22 shows the results of ELISA for L1h-specific antibodies and antibody titer in sera of mice immunized with pcL1h and pcE5(Group 1 (G1): administered intradermally with pcL1h+pcE5+LTB Group 2 (G2): administered intradermally with pcL1h+pcE5 Group 3 (G3): administered intramuscularly with pcL1h+pcE5+LTB Group 4 (G4): administered intramuscularly with pcL1h+pcE5 Group 5 (G5, a negative control): administered intradermally with pcDNA; Group 6 (G6, a negative control): administered intramuscularly with pcDNA);

FIG. 23 shows the results of ELISA for L1-specific antibodies according to a various combination of L1, L2 and E5 (Group (G1) and Group 2 (G2): administered intradermally and intramuscularly, respectively, with pcL1h+pcL2h Group 3 (G3) and Group 4 (G4): administered intradermally and intramuscularly, respectively, with pcE5 alone; Group 5 (G5) and Group 6 (G6): administered intradermally and intramuscularly, respectively, with pcL1h+pcE5 Group 7 (G7) and Group 8 (G8): administered intradermally and intramuscularly, respectively, with pcL1h+pcL2h+pcE5 Group 9 (G9) and Group 10 (G10), as negative controls: administered intradermally and intramuscularly, respectively, with an empty pcDNA plasmid);

FIG. 24 shows the results of a neutralization assay in mice immunized with pcL1h and pcE5 (Group 1: administered intradermally with pcL1h+pcE5+LTB Group 2: administered intradermally with pcL1 h+pcE5 Group 3: administered intramuscularly with pcL1h+pcE5+LTB Group 4: administered intramuscularly with pcL1h+pcE5 Groups 5 and 6, as negative controls: administered intradermally and intramuscularly, respectively, with an empty pcDNA plasmid);

FIG. 25 is a photograph showing the results of an ELISpot assay in mice immunized intradermally with pcL1h and pcE5 (Group 1: pcL1h+pcE5 Group 2: pcL1h+pcE5+pcIL1 Group 3: pcL1h+pcE+pcGM-CSF Group 4: negative control);

FIG. 26 is a graph showing ELISpot data that are represented by the number of spots, indicating IFN-gamma secreting cells;

FIG. 27 shows the results of an E5-specific CTL assay in mice immunized with pcL1h and pcE5 and FIG. 28 shows the results of an L1-specific CTL assay in mice immunized with pcL1h and pcL2h.

BEST MODE

In one aspect, the present invention relates to a DNA vaccine for treating cervical cancer comprising an HIV E5 gene.

As used herein, the term "therapeutic vaccine" refers to a vaccine for treating HPV infection, which induces a cell-mediated immune response, cytolytic activity, targeted against epithelial cells from persons infected with HPV and thus controls or suppress the growth of existing HPV-associated tumors.

In one embodiment of the present invention, the therapeutic vaccine was prepared as follows. PCR primers specific to the HPV E5 gene were designed. A PCR product, obtained through PCR, was cloned into a suitable expression vector that was in turn transformed into a host cell to mass-produce the E5 gene. The host cell may be any prokaryotic or eukaryotic cell. For convenience, the E5 gene may be mass-produced using prokaryotic cells such as E. coli.

In another aspect, the present invention relates to an antigen combination DNA vaccine for preventing or treating cervical cancer.

As used herein, the term "antigen combination vaccine" refers to a vaccine that has both therapeutic and prophylactic effects, and that includes the E5 gene for therapeutic effects and another DNA gene for prophylactic efficacy. Preferably, the DNA gene for prophylactic efficacy may be a gene encoding the capsid L1 and/or L2 protein of HPV.

The antigen combination vaccine according to the present invention may be prepared either by inserting individually the L1 and/or L2 gene, for prophylactic efficacy, and the E5 gene, for therapeutic efficacy, into separate plasmids and mixing the separate plasmids each carrying the gene, or by combining the genes into a single plasmid capable of expressing the genes at the same time. Preferably, the antigen combination vaccine according to the present invention may be prepared by inserting the E5 gene and the L1 and/or L2 gene into separate plasmids and mixing the separate plasmids.

In a preferred embodiment, high-risk HPV type 16 was used, but the present invention is not limited thereto, and an E5 gene from other HPV types is also available. In addition to type 16, high-risk HPV genotypes, which have high potential for progression to cervical cancer, include 18, 26, 30, 31, 33, 34, 35, 39, 45, 51, 52, 53, 56, 58, 59, 61, 66, 67, 69, 70, and 73. Hence, the DNA vaccine for preventing and treating cervical cancer may include an E5 gene selected from the group consisting of the high-risk HPV genotypes and an L1 and/or L2 gene.

The E5 gene and the L1 and/or L2 gene may be codon-optimized to increase their expression in mammalian cells. In a detailed embodiment, a nucleic acid having the nucleotide sequence of SEQ ID No. 10 was used as a codon-optimized L1 gene (L1h), and another nucleic acid, having the nucleotide sequence of SEQ ID No. 12, was used as a codon-optimized L2 gene (L2h). As a codon-optimized E5 gene, a nucleic acid having the nucleotide sequence of SEQ ID No. 14 was used.

In a detailed embodiment, the antigen combination vaccine was prepared as follows. HPV-16 L1 and L2 genes were obtained from p16L1h and p16L2h plasmids, which were provided for research purposes from Deutsches Krebsforschungszentrum (Im Neuenheimer Feld 280, D-69120 Heidelberg, Germany), and were cloned into a mammalian expression vector pcDNA3.1(−) (Invitrogen, USA), thereby obtaining pcDNA-L1h and pcDNA-L2h plasmids. The plasmids were transformed into E. coli to obtain plasmids bearing the L1 and L2 genes in large amounts (Examples 1-1, 1-2 and 6). In the present specification, the pcDNA-L1h and pcDNA-L2h plasmids are interchangeably used for convenience with pcL1h and pcL1h, respectively.

In addition, HPV-16 E5 gene was prepared as follows. PCR primers were designed using the known genetic information so as to amplify the full-length gene sequence. A PCR product, obtained through overlapping PCR, was cloned into a mammalian expression vector pcDNA3.1A (Invitrogen, USA), thereby obtaining a pcDNA-E5 plasmid. E. coli was transformed with the plasmid and cultured (Examples 1-3 and 6). In the present specification, the pcDNA-E5 plasmid is interchangeably used for convenience with pcE5, pcE5(opti) or pcDNA-E5(opti).

The immunization with a mixture of pcE5 and pcL1h plasmids induced higher L1-specific antibody responses (see, FIG. 16), and also induced cytotoxic T lymphocytes (CTL) having cytolytic activity specific to the E5 oncoprotein and the capsid L1 protein (FIG. 19, etc.).

These results indicated that the present DNA vaccine, comprising an E5 gene, could be a therapeutic vaccine against cervical cancer, and that, when it further includes an L1 and/or L2 gene, it has potential as an antigen combination DNA vaccine having both therapeutic and prophylactic effects.

In a further aspect, the present invention provides a vaccine composition for preventing or treating cervical cancer comprising the above vaccine and a pharmaceutically acceptable carrier or adjuvant.

As used herein, the term "adjuvant" refers to a compound that enhances the immune response to an antigen or strengthens specific activity of cells in the immune system in a subject receiving the antigen when administered into individuals or upon an in vitro test. Any adjuvant known in the art to induce cellular immunity and to be safe is available. IL-15, GM-CSF and LTB were used as adjuvants in the practice of the present invention, but the present invention is not limited thereto.

The vaccine composition, including a pharmaceutically acceptable carrier, may be formulated for use in human or veterinary medicine, and may be administered via various routes, including orally, intraperitoneally, intravenously, intramuscularly, subcutaneously and intradermally. Preferably, the composition is formulated as an injectable preparation. Particularly preferably, the composition is injected intradermally.

In a detailed embodiment, when the vaccine according to the present invention was injected intramuscularly or administered intradermally using a common tattoo device, the intradermal administration using the tattoo device induced a higher immune response.

Thus, in yet another aspect, the present invention provides a method of injecting the vaccine composition intradermally to enhance the immunogenicity of the vaccine, and a vaccine composition suitable for intradermal administration.

Injectable preparations may be prepared using physiological saline, aqueous solutions such as Ringer s solution, and non-aqueous solutions, such as vegetable oils, high fatty acid esters (e.g., ethyl oleic acid, etc.), alcohols (e.g., ethanol, benzylalcohol, propylene glycol and glycerin, etc.). The injectable preparations may be supplemented with pharmaceutical carriers, which are exemplified by a stabilizer for preventing degeneration (e.g., ascorbic acid, sodium hydrogen sulfite, sodium pyrosulfite, BHA, tocopherol, EDTA, etc.), an emulsifier, a buffering agent for pH control, and a preservative for inhibiting microbial growth (e.g., phenylmercury nitrate, thimerosal, benzalkonium chloride, phenol, cresol, benzylalcohol, etc.).

The present composition may be administered in a pharmaceutically effective amount. The term "pharmaceutically effective amount", as used herein, refers to an amount sufficient for displaying a vaccine effect but not causing side effects or severe or excessive immune responses. The accurate dosage may vary depending on the antigen to be administered, and may be readily determined by those skilled in the art according to factors known in medicine, including the patient s age, weight, health state, gender and sensitivity to drugs, administration routes, and administration methods. The composition may be administered in a single dose or in several divided doses. Preferably, the vaccine composition of the present invention may be administered into experimental mice in a dose ranging from 10 µg to 20 µg.

In still another aspect, the present invention provides a cell line stably expressing the E5 oncoprotein. The cell line according to the present invention was prepared by transforming an E5 gene into TC-1 cells (obtained for research purpose from the School of Medicine, Johns Hopkins University) (Example 4). Due to its stable and continuous E5 protein expression, the cell line may be useful in the establishment of a tumor model system, and particularly in the detection of therapeutic or prophylactic effects against HPV infection or screening for the development of therapeutic drugs against HPV infection. Also, the cell line can be used as a sample for the development of biomarkers, which enable the diagnosis and prognosis of cervical cancer using genomics and/or proteomics.

Mode for Invention

A better understanding of the present invention may be obtained through the following examples, which are set forth to illustrate, but are not to be construed as the limit of, the present invention.

EXAMPLE 1

Plasmid DNA Constructs 1-1. HPV-16 L1 plasmid construction

Figures 5, 6:
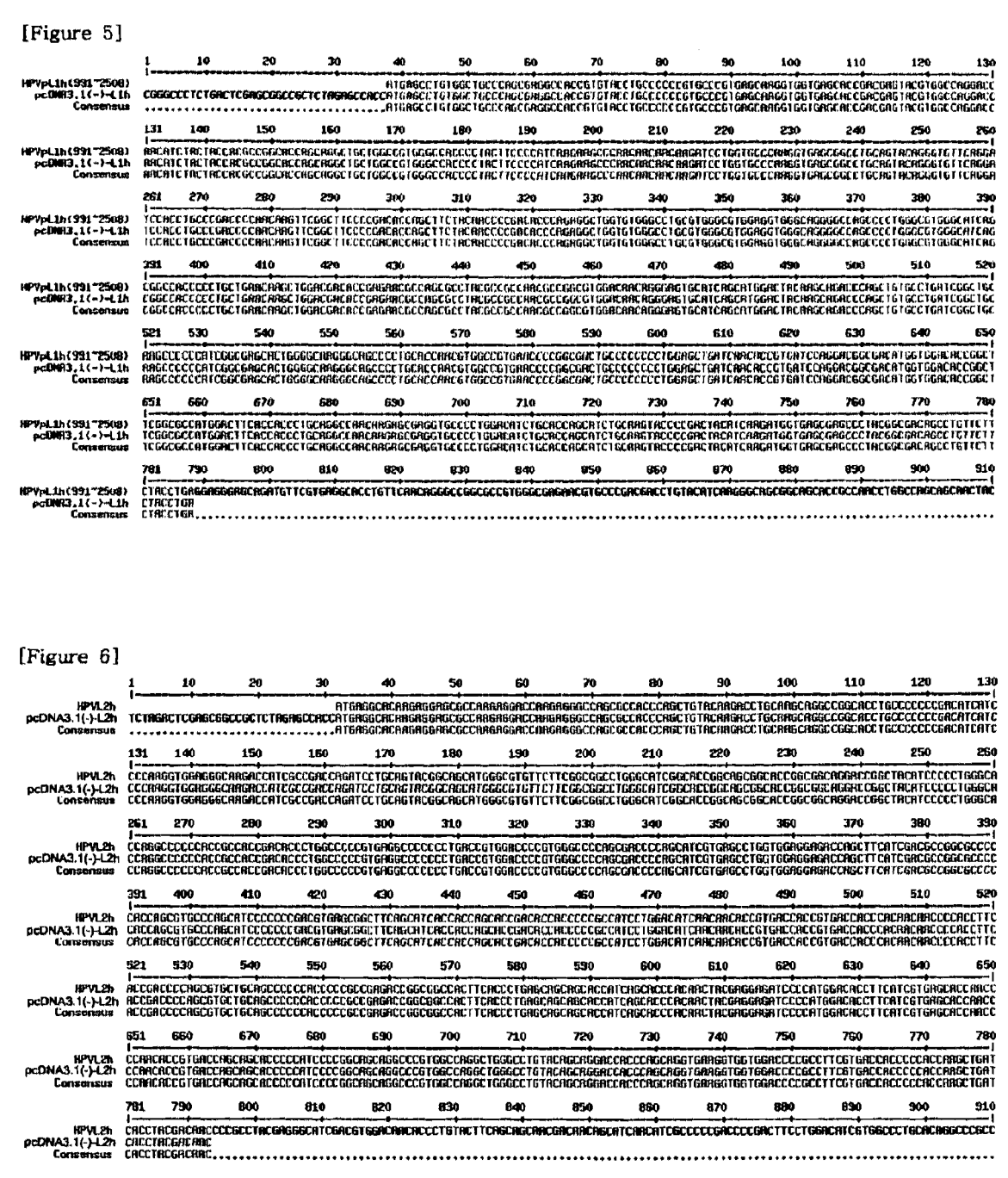

The HPV-16 L1 gene was obtained from a p16L1h plasmid, which was provided for research purpose from Deutsches Krebsforschungszentrum (Im Neuenheimer Feld 280, D-69120 Heidelberg, Germany). The L1 gene carried in the plasmid, L1h, had been codon-optimized to improve its expression in mammalian cells. The p16L1h plasmid was digested with NotI and HindIII to excise the L1 h region. The L1h was inserted into a mammalian expression vector pcDNA3.1(−) (Invitrogen, USA), thereby obtaining pcDNA-L1h plasmid. FIG. 1 schematically shows the process of constructing the L1 expression vector. For conveniences, the pcDNA-L1h plasmid was also designated simply as "pcL1h" The pcL1h plasmid was then transformed into E. coli, and successful transformation was confirmed using restriction endonuclease digestion and gel electrophoresis (FIG. 3). The nucleotide sequence of the L1h gene was aligned with that of p16L1h (FIG. 5). The nucleotide sequence of the L1h gene is shown in SEQ ID No. 10, and its encoded amino acid sequence is shown in SEQ ID No. 11.

1-2. HPV-16 L2 Plasmid Construction

The HPV-16 L2 gene was obtained from the p16L2h plasmid, which was provided for research purposes from Deutsches Krebsforschungszentrum (Im Neuenheimer Feld 280, D-69120 Heidelberg, Germany). The L2 gene carried in the plasmid, L2h, had been codon-optimized to improve its expression in mammalian cells. The p16L2h plasmid was digested with NotI and HindIII to excise the L2h region. TheL2h was inserted into a mammalian expression vector pcDNA3.1(−) (Invitrogen, USA), thereby obtaining a pcDNA3.1(1)-L2h plasmid. FIG. 2 schematically shows the process of constructing the L2 expression vector. For convenience, the pcDNA3.1(1)-L2h plasmid was also designated simply "pcL2h". The pcL2h plasmid was then transformed into E. coli, and successful transformation was confirmed using restriction endonuclease digestion and gel electrophoresis (FIG. 4). The nucleotide sequence of the L2h gene was aligned with that of pcL2h (FIG. 6). The nucleotide sequence of the L2h gene is shown in SEQ ID No. 12, and its encoded amino acid sequence is shown in SEQ ID No. 13.

1-3. HPV-0.16 E5 Plasmid Construction

PCR primers were designed so as to amplify the full-length sequence of the HPV-16 E5 gene, and their sequences are shown in SEQ ID Nos. 8 and 9. For overlapping PCR, primers of SEQ ID Nos. 1 to 7 were designed and synthesized based on the nucleotide sequence described in Disbrow et al., Virology, 2003, Jun. 20, 311(1):105-14. The primers SEQ ID Nos. 1 to 7 were codon-optimized to increase mammalian cell expression.

```
HP5Hu.s1 (82mer):
                                        (SEQ ID No. 1)
5'-ATGACAAATCTGGATACTGCATCCACAACACTGCTGGCGTG

CTTTCTGCTGTGCTTTTGTGTGCTGCTGTGTGTCTGCCTGC-3'

HP5Hu.s2 (86mer)
                                        (SEQ ID No. 2)
5'-TGATCAGGCCCCTGCTGCTGTCTGTGTCTACATACACATCC

CTGATCATCCTGGTGCTGCTGCTGTGGATCACAGCAGCCTCTGC

C-3'

HP5Hu.s3 (81mer)
                                        (SEQ ID No. 3)
5'-TTTAGGTGTTTTATTGTGTATATTATCTTTGTGTATATCCC

ACTGTTTCTGATCCATACACATGCACGCTTTCTGATTACA-3'

HP5Hu.as1 (43mer)
                                        (SEQ ID No. 4)
5'-TGTAATCAGAAAGCGTGCATGTGTATGGATCAGAAACAG

TGGG-3'

HP5Hu.as2 (85mer)
                                        (SEQ ID No. 5)
5'-ATATACACAAAGATAATATACACAATAAAACACCTAAAG

GCAGAGGCTGCTGTGATCCACAGCAGCAGCACCAGGATGATC

AGGG-3'
```

-continued

```
HP5Hu.as3 (81mer)
                                            (SEQ ID No. 6)
5'-ATGTGTATGTAGACACAGACAGCAGCAGGGGCCTGAT

CAGCAGGCAGACACACAGCAGCACACAAAAGCACAGCAGAA

AGC-3'

HP5Hu.as4 (40mer)
                                            (SEQ ID No. 7)
5'-ACGCCAGCAGTGTTGTGGATGCAGTATCCAGATTT

GTCAT-3'
```

The primers of SEQ ID Nos. 1 to 7 were purified through PAGE. In order to obtain an insert to be cloned into pcDNA, the seven purified primers and the primers shown in FIG. 7 (SEQ ID Nos. 8 and 9) were pooled in one PCR tube, and allowed to anneal to each other, ligate and be amplified through PCR using Ampligase Thermostable DNA Ligase (Epicentre, USA). Thus, the artificially synthesized PCR product was also codon-optimized to improve its expression in mammalian cells.

The PCR product thus obtained was cloned into pcDNA3.1A (Invitrogen, USA), thereby obtaining pcDNA-E5 plasmid. This plasmid was transformed into *E. coli*. Plasmid DNA was isolated from the transformed *E. coli* cells, and subjected to restriction endonuclease digestion and gel electrophoresis, thereby confirming successful cloning (FIG. 8). As shown in FIG. 8, the E5 gene was about 250 bp long. The nucleotide sequence of the E5 gene was determined and compared with the published nucleotide sequence of codon-optimized HPV-16 E5, which is described in G. L. Disbrow et al., Virology 311 (2003), 105-114 (FIG. 9). The determined nucleotide sequence of the E5 gene is shown in SEQ ID No. 4, and its encoding amino acid sequence is shown in SEQ ID No. 15. For convenience, the pcDNA-E5 plasmid also is designated as pcE5, pcE5(opti) or pcDNA-E5(opti).

EXAMPLE 2

Indirect Immunofluorescence Assay (IFA) for the Detection of L1h and E5 expression 2-1. IFA for L1h (ucL1h)<

The pcL1h prepared in Example 1-1 was transiently transfected into Rhabdomyosarcoma (RD) cells (ATCC Cat No. CCL136 USA) using Fugene 6. After two days, an indirect immunofluorescence assay (IFA) was performed using an HPV 16 L1-specific CamVir-1 antibody as the primary antibody and Alexa Fluor 488-labeled anti-mouse IgG as the secondary antibody. Unlike a negative control, fluorescence in pcL1h-transfected cells was strongly localized in the nuclei (FIG. 10).

2-2. IFA for E5 (pcE5)<

The pcE5, prepared in Example 1-3, was transiently transfected into RD cells using Fugene 6, as described in Example 2-1. After two days, IFA was performed using mouse anti-His (Invitrogen, USA) as the primary antibody and Alexa Fluor 488-labeled anti-mouse IgG as the secondary antibody. Compared to a negative control, specific fluorescence was seen in the cytoplasm of transfected cells, indicating that the E5 protein was expressed in the cytoplasm (FIG. 11).

EXAMPLE 3

Western Blotting for L1h and E5

3-1. Western Blotting for L1h (pcL1h)

The pcL1h plasmid was transiently transfected into 293TT cells using electroporation. After two days, cells were lysed with lysis buffer ($MgCl_2$, Brij58, Benzonase, Plasmid-Safe ATP-dependent DNase), and the thus-obtained cell lysates were subjected to Western blot analysis. Western blotting was carried out using CamVir-1 antibody as the primary antibody and mouse IgG-HRP (Sigma, USA, 1:2000) as the secondary antibody. An L1h-specific band was detected in about 53 kDa (lane 2, FIG. 12), indicating that the pcL1h plasmid expressed L1h in vitro. In FIG. 12, lane 1 is a Western blot for the lysate of cells transfected with the p16L1h plasmid carrying L1h gene, which was obtained from Germany, and lane 3 is a Western blot for pseudovirion L1 virus-like particles (VLPs) containing a SEAP (Secreted Enhanced Alkaline Phosphatase) reporter gene, which were purified through separation using Opti-Prep.

3-2. Western Blotting for E5 (pcE5)

The pcE5 plasmid was transiently transfected into 293TT cells using a calcium phosphate method. After two days, cells were lysed with an RIPA buffer, and the cell lysates thus obtained were analyzed using Western blotting. Western blotting was carried out using anti-V5 (Invitrogen, USA, 1:5000) as the primary antibody and mouse IgG-HRP (Sigma, USA, 1:2000) as the secondary antibody. Compared to a negative control, transfected with pcDNA, an E5-specific band was detected in about 13 kDa (FIG. 13).

EXAMPLE 4

Establishment of TC-1/E5 Stable Cell Line

TC-1 cells, obtained for research purposes from the School of Medicine, Johns Hopkins University, were co-transfected with pcE5(opti), prepared in Example 1-3, and pPURO plasmid (Clontech, US) using Fugene-6. The selection of stable transfectants was started with 1.5 μg/ml of puromycin two days post-transfection. From the thus selected TC-1/E5 clone, total RNA was isolated using trizol, and RT-PCR was carried out using E5-specific primers. The resulting PCR reaction mixture was electrophoresed, and an E5-specific band of about 250 bp was observed (FIG. 14).

The stable expression of E5 in the selected TC-1/E5 clone was further confirmed in the protein level using IFA and Western blotting. As shown in FIGS. 15 and 16, the sustained and stable expression of E5 in the cell clone was observed. The cell line, enabling the stable expression of HPV E5 protein, may be very useful in the establishment of a tumor model system, as described in the following example, and particularly in the development of therapeutic and prophylactic vaccines against HPV infection and the detection of efficacies of such vaccines. Also, the established cell line can be used as a sample for the development of biomarkers that enable the diagnosis and prognosis of cervical cancer using genomics and/or proteomics. Thus, the TC-1/E5#7 cell line was deposited at the Korean Cell Line Bank (KCLB) (Cancer Research Institute, Seoul National University) on Oct. 19, 2006, and assigned accession number KCLRF-BP-00140

EXAMPLE 5

Establishment of Tumor Model System

A mouse tumor model system was established in order to evaluate the tumor regression and prophylactic effects of the HPV L1h/E5 DNA vaccine. The TC-1/E5 cell line, established in Example 4, was injected subcutaneously into the hind legs of C57BL/6 mice, and tumor formation was observed (FIGS. 17 and 18).

EXAMPLE 6

Immunization and ELISA

*E. coli* was transformed with the plasmids prepared in Example 1 and cultured for large-scale plasmid preparation. Plasmid DNA was purified using a DNA Endotoxin-free Giga prep kit (Qiagen), thereby obtaining pcE5(opti), pcL1h and pcL2h in large amounts. Mice were then immunized with the plasmid DNA.

Three immunization experiments were conducted as described in Tables 1 to 3, below. For the first mouse immunization, as described in Table 1, twenty-four C57BL/6 mice (4-week old) were divided into four groups, each group consisting of six mice. For the second mouse immunization, as described in Table 2, twenty-four C57BL/6 mice (4-week old) were divided into six groups, each group consisting of four mice. For the third mouse immunization, as described in Table 3, forty C57BL/6 mice (4-week old) were divided into 10 groups, each group consisting of four mice. Mice were immunized intradermally using a tattoo device, or were injected intramuscularly. For more detailed information for immunization, see the following tables and FIGS. 19 to 21.

TABLE 1

| | Immunogen |
|---|---|
| Group 1(6) | pcL1h + pCE5(opti) |
| Group 2(6) | pcL1h + pCE5(opti) + pcIL15 |
| Group 3(6) | pcL1h + pCE5(opti) + pcGM-CSF |
| Group 4(6) | PBS |

TABLE 2

| | Immunogen | Adjuvant |
|---|---|---|
| Group 1 | pcL1h + pcE5 DNA (intradermal) | LTB 10 µg |
| Group 2 | pcL1h + pcE5 DNA (intradermal) | No |
| Group 3 | pcL1h + pcE5 DNA (intramuscular) | LTB 10 µg |

TABLE 2-continued

| | Immunogen | Adjuvant |
|---|---|---|
| Group 4 | pcL1h + pcE5 DNA (intramuscular) | No |
| Group 5 | pcDNA (intradermal) | No |
| Group 6 | pcDNA (intramuscular) | No |

TABLE 3

| | Immunogen and Immunization Route |
|---|---|
| Group 1 | pcL1h + pcL2h DNA (intradermal) |
| Group 2 | pcL1h + pcL2h DNA (intramuscular) |
| Group 3 | pcE5 DNA (intradermal) |
| Group 4 | pcE5 DNA (intramuscular) |
| Group 5 | pcL1h + pcE5 DNA (intradermal) |
| Group 6 | pcL1h + pcE5 DNA (intramuscular) |
| Group 7 | pcL1h + pcL2h + pcE5 DNA (intradermal) |
| Group 8 | pcL1h + pcL2h + pcE5 DNA (intramuscular) |
| Group 9 | pcDNA (intradermal) |
| Group 10 | pcDNA (intramuscular) |

As described hereinbefore, the immunization with the antigen combination vaccine, comprising an E5 gene and an L1/L2 gene, started to induce L1-specific antibodies 4 weeks after the first injection. A CTL assay, performed 8 weeks after the first injection, revealed that the vaccine induced CTL cells having E5 oncoprotein-specific cytolytic activity, and that the antibodies had neutralizing activity of about 70%. In addition, the intradermal injection of the combination DNA vaccine in a small amount of DNA (10 µg/dose or 10 µg/10 µl volume) induced HPV L1-specific neutralizing antibodies and E5-specific CTL cells.

INDUSTRIAL APPLICABILITY

Thus, the combination vaccine of an HPV E5 gene and an L1 and/or L2 gene according to the present invention may be very effective in the treatment and prevention of cervical cancer.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for treating or preventing invasive cervical cancer comprising: administering to an individual in need thereof a vaccine composition comprising an E5 gene and an L1 gene of human papillomavirus (HPV), wherein the L1 consists of a codon-optimized nucleotide sequence represented by SEQ ID NO:10 and the E5 gene consists of a codon-optimized nucleotide sequence represented by SEQ ID NO:14.

2. The method of claim 1, further comprising a gene encoding HPV L2, wherein the L2 gene consists of a codon-optimized nucleotide sequence represented by SEQ ID NO:12.

3. The method as set forth in claim 1, wherein the E5 and L1 genes are carried in separate plasmids for independent expression.

4. The method as set forth in claim 2, wherein the E5, L1 and L2 genes are carried in separate plasmids for independent expression.

5. The method as set forth in claim 1, wherein the vaccine composition further comprising an adjuvant, wherein the adjuvant is selected from LTB, IL-15 or GM-CSF.

6. The method as set forth in claim 1, wherein the vaccine composition is administered intradermally or intramuscularly.

7. The vaccine composition method as set forth in claim 6, wherein the vaccine composition is administered intradermally.

8. The method as set forth in claim 7, which is wherein the vaccine composition is administered intradermally using a tattoo device.

9. The method of claim 1, wherein said invasive cervical cancer is uterine cervical cancer.

* * * * *

SEQUENCE LISTING

```
<160> NUMBER OF SEQ ID NOS: 15

<210> SEQ ID NO 1
<211> LENGTH: 82
<212> TYPE: DNA
<213> ORGANISM: Artificial Sequence
<220> FEATURE:
<223> OTHER INFORMATION: HP5Hu.s1:82mer(primer)

<400> SEQUENCE: 1
atgacaaatc tggatactgc atccacaaca ctgctggcgt gctttctgct gtgcttttgt    60
gtgctgctgt gtgtctgcct gc                                             82

<210> SEQ ID NO 2
<211> LENGTH: 86
<212> TYPE: DNA
<213> ORGANISM: Artificial Sequence
```

```
<220> FEATURE:
<223> OTHER INFORMATION: HP5Hu.s2: 86mer(Primer)

<400> SEQUENCE: 2
tgatcaggcc cctgctgctg tctgtgtcta catacacatc cctgatcatc ctggtgctgc    60
tgctgtggat cacagcagcc tctgcc                                         86

<210> SEQ ID NO 3
<211> LENGTH: 81
<212> TYPE: DNA
<213> ORGANISM: Artificial Sequence
<220> FEATURE:
<223> OTHER INFORMATION: HP5Hu.s3: 81mer(Primer)

<400> SEQUENCE: 3
tttaggtgtt ttattgtgta tattatcttt gtgtatatcc cactgtttct gatccataca    60
catgcacgct ttctgattac a                                              81

<210> SEQ ID NO 4
<211> LENGTH: 43
<212> TYPE: DNA
<213> ORGANISM: Artificial Sequence
<220> FEATURE:
<223> OTHER INFORMATION: HP5Hu.as1: 43mer(Primer)

<400> SEQUENCE: 4
tgtaatcaga aagcgtgcat gtgtatggat cagaaacagt ggg                      43

<210> SEQ ID NO 5
<211> LENGTH: 85
<212> TYPE: DNA
<213> ORGANISM: Artificial Sequence
<220> FEATURE:
<223> OTHER INFORMATION: HP5Hu.as2: 85mer(Primer)

<400> SEQUENCE: 5
atatacacaa agataatata cacaataaaa cacctaaagg cagaggctgc tgtgatccac    60
agcagcagca ccaggatgat caggg                                          85

<210> SEQ ID NO 6
<211> LENGTH: 81
<212> TYPE: DNA
<213> ORGANISM: Artificial Sequence
<220> FEATURE:
<223> OTHER INFORMATION: HP5Hu.as3: 81mer(Primer)

<400> SEQUENCE: 6
atgtgtatgt agacacagac agcagcaggg gcctgatcag caggcagaca cacagcagca    60
cacaaaagca cagcagaaag c                                              81

<210> SEQ ID NO 7
<211> LENGTH: 40
<212> TYPE: DNA
<213> ORGANISM: Artificial Sequence
<220> FEATURE:
<223> OTHER INFORMATION: HP5Hu.as4: 40mer(Primer)

<400> SEQUENCE: 7
acgccagcag tgttgtggat gcagtatcca gatttgtcat                          40

<210> SEQ ID NO 8
<211> LENGTH: 40
<212> TYPE: DNA
<213> ORGANISM: Artificial Sequence
```

```
<220> FEATURE:
<223> OTHER INFORMATION: HPV16 E5 sense primer

<400> SEQUENCE: 8
gccgccaagc ttgccgccac catgacaaat ctggatactg                          40

<210> SEQ ID NO 9
<211> LENGTH: 33
<212> TYPE: DNA
<213> ORGANISM: Artificial Sequence
<220> FEATURE:
<223> OTHER INFORMATION: HPV16 E5 anti-sense primer

<400> SEQUENCE: 9
atcgggctcg agttatgtaa tcagaaagcg tgc                                 33

<210> SEQ ID NO 10
<211> LENGTH: 1518
<212> TYPE: DNA
<213> ORGANISM: Artificial Sequence
<220> FEATURE:
<223> OTHER INFORMATION: HPV L1h codon optimized sequence

<400> SEQUENCE: 10
atgagcctgt ggctgcccag cgaggccacc gtgtacctgc cccccgtgcc cgtgagcaag      60
gtggtgagca ccgacgagta cgtggccagg accaacatct actaccacgc cggcaccagc     120
aggctgctgg ccgtgggcca ccctacttc cccatcaaga agcccaacaa caacaagatc     180
ctggtgccca agtgagcgg cctgcagtac agggtgttca ggatccacct gcccgacccc     240
aacaagttcg gcttccccga caccagcttc tacaaccccg acacccagag gctggtgtgg     300
gcctgcgtgg gcgtggaggt gggcaggggc cagccctgg gcgtgggcat cagcggccac     360
cccctgctga caagctgga cgacaccgag aacgccagcg cctacgccgc caacgccggc     420
gtggacaaca gggagtgcat cagcatggac tacaagcaga cccagctgtg cctgatcggc     480
tgcaagcccc ccatcggcga gcactgggc aagggcagcc cctgcaccaa cgtggccgtg     540
aaccccggcg actgccccc cctggagctg atcaacaccg tgatccagga cggcgacatg     600
gtggacaccg gcttcggcgc catggacttc accaccctgc aggccaacaa gagcgaggtg     660
cccctggaca tctgcaccag catctgcaag taccccgact acatcaagat ggtgagcgag     720
ccctacggcg acagcctgtt cttctacctg aggagggagc agatgttcgt gaggcacctg     780
ttcaacaggg ccggcgccgt gggcgagaac gtgcccgacg acctgtacat caagggcagc     840
ggcagcaccg ccaacctggc cagcagcaac tacttcccca cccccagcgg cagcatggtg     900
accagcgacg cccagatctt caacaagccc tactggctgc agagggccca gggccacaac     960
aacggcatct gctgggggcaa ccagctgttc gtgaccgtgg tggacaccac caggagcacc    1020
aacatgagcc tgtgcgccgc catcagcacc agcgagacca cctacaagaa caccaacttc    1080
aaggagtacc tgaggcacgg cgaggagtac gacctgcagt tcatcttcca gctgtgcaag    1140 atcacccctga ccgccgacgt gatgacctac atccacagca tgaacagcac catcctggag    1200
gactggaact tcggcctgca gccccccccc ggcggcaccc tggaggacac ctacaggttc    1260
gtgaccagcc aggccatcgc ctgccagaag cacacccccc cgcccccaa ggaggacccc    1320 ctgaagaagt acaccttctg ggaggtgaac ctgaaggaga gttcagcgc cgacctggac    1380 cagttccccc tgggcaggaa gttcctgctg caggccggcc tgaaggccaa gcccaagttc    1440
acctggggca gaggaaggc caccccccacc accagcagca ccagcaccac cgccaagagg    1500
aagaagagga agctgtga                                                  1518
```

<210> SEQ ID NO 11
<211> LENGTH: 505
<212> TYPE: PRT
<213> ORGANISM: Human Papiloma Virus

<400> SEQUENCE: 11

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

```
Ala Asp Val Met Thr Tyr Ile His Ser Met Asn Ser Thr Ile Leu Glu
385                 390                 395                 400

Asp Trp Asn Phe Gly Leu Gln Pro Pro Gly Thr Leu Glu Asp
            405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
            485                 490                 495

Thr Ala Lys Arg Lys Arg Lys Leu
            500                 505

<210> SEQ ID NO 12
<211> LENGTH: 1422
<212> TYPE: DNA
<213> ORGANISM: Artificial Sequence
<220> FEATURE:
<223> OTHER INFORMATION: HPV L2 codon optimized sequence

<400> SEQUENCE: 12
atgaggcaca agaggagcgc caagaggacc aagagggcca gcgccaccca gctgtacaag        60
acctgcaagc aggccggcac ctgccccccc gacatcatcc caaggtggga gggcaagacc       120
atcgccgacc agatcctgca gtacggcagc atgggcgtgt tcttcggcgg cctgggcatc       180
ggcaccggca gcggcaccgg cggcaggacc ggctacatcc ccctgggcac caggcccccc       240
accgccaccg acaccctggc ccccgtgagg ccccccctga ccgtggaccc cgtgggcccc       300
agcgacccca gcatcgtgag cctggtggag gagaccagct tcatcgacgc cggcgccccc       360
accagcgtgc ccagcatccc ccccgacgtg agcggcttca gcatcaccac cagcaccgac       420 accaccccg ccatcctgga catcaacaac accgtgacca ccgtgaccac ccacaacaac       480
cccaccttca ccgaccccag cgtgctgcag ccccccaccc ccgccgagac cggcggccac       540
ttcaccctga gcagcagcac catcagcacc cacaactacg aggagatccc catggacacc       600
ttcatcgtga gcaccaaccc caacaccgtg accagcagca ccccatccc cggcagcagg       660 cccgtggcca ggctgggcct gtacagcagg accacccagc aggtgaaggt ggtggacccc       720
gccttcgtga ccacccccac caagctgatc acctacgaca ccccgccta cgagggcatc       780 gacgtggaca caccctgta cttcagcagc aacgacaaca gcatcaacat cgcccccgac       840
cccgacttcc tggacatcgt ggccctgcac aggcccgccc tgaccagcag gaggaccggc       900
atcaggtaca gcaggatcgg caacaagcag accttgagga ccaggagcgg caagagcatc       960
ggcgccaagg tgcactacta ctacgacttg agcaccatcg accccgccga ggagatcgag      1020
ctgcagacca tcacccccag cacttacacc accaccagca cgccgccag ccccaccagc      1080 atcaacaacg gcctgtacga catctacgcc gacgacttca tcaccgacac cagcaccacc      1140
cccgtgccca gcgtgcccag caccagcctg agcggctaca tccccgccaa ccaccatc      1200 cccttcggtg gcgcctacaa catccccctg gtgagcggcc ccgacatccc catcaacatc      1260
accgaccagg cccccagcct gatccccatc gtgcccggca gccccagta ccatcatc      1320 gccgacgccg gcgacttcta cctgcacccc agctactaca tgctgaggaa gaggaggaag      1380
```
aggctgccct acttcttcag cgacgtgagc ctggccgcct ga                1422

<210> SEQ ID NO 13
<211> LENGTH: 473
<212> TYPE: PRT
<213> ORGANISM: Human Papiloma Virus

<400> SEQUENCE: 13

Met Arg His Lys Arg Ser Ala Lys Arg Thr Lys Arg Ala Ser Ala Thr
 1               5                  10                  15

Gln Leu Tyr Lys Thr Cys Lys Gln Ala Gly Thr Cys Pro Pro Asp Ile
             20                  25                  30

Ile Pro Lys Val Glu Gly Lys Thr Ile Ala Asp Gln Ile Leu Gln Tyr
         35                  40                  45

Gly Ser Met Gly Val Phe Phe Gly Gly Leu Gly Ile Gly Thr Gly Ser
     50                  55                  60

Gly Thr Gly Gly Arg Thr Gly Tyr Ile Pro Leu Gly Thr Arg Pro Pro
 65                  70                  75                  80

Thr Ala Thr Asp Thr Leu Ala Pro Val Arg Pro Pro Leu Thr Val Asp
                 85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Leu Ser Thr Ile Asp Pro Ala
                325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
        355                 360                 365

-continued

```
Tyr Ala Asp Asp Phe Ile Thr Asp Thr Ser Thr Thr Pro Val Pro Ser
    370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
                420                 425                 430

Gly Ser Pro Gln Tyr Thr Ile Ile Ala Asp Ala Gly Asp Phe Tyr Leu
            435                 440                 445

His Pro Ser Tyr Tyr Met Leu Arg Lys Arg Arg Lys Arg Leu Pro Tyr
    450                 455                 460

Phe Phe Ser Asp Val Ser Leu Ala Ala
465                 470

<210> SEQ ID NO 14
<211> LENGTH: 252
<212> TYPE: DNA
<213> ORGANISM: Artificial Sequence
<220> FEATURE:
<223> OTHER INFORMATION: HPV E5 codon optimized sequence

<400> SEQUENCE: 14
atgacaaatc tggatactgc atccacaaca ctgctggcgt gctttctgct gtgcttttgt      60
gtgctgctgt gtgtctgcct gctgatcagg cccctgctgc tgtctgtgtc tacatacaca     120
tccctgatca tcctggtgct gctgctgtgg atcacagcag cctctgcctt taggtgtttt     180
attgtgtata ttatctttgt gtatatccca ctgtttctga tccatacaca tgcacgcttt     240
ctgattacat aa                                                         252

<210> SEQ ID NO 15
<211> LENGTH: 83
<212> TYPE: PRT
<213> ORGANISM: Human Papiloma Virus

<400> SEQUENCE: 15

Met Thr Asn Leu Asp Thr Ala Ser Thr Thr Leu Leu Ala Cys Phe Leu
1               5                   10                  15

Leu Cys Phe Cys Val Leu Leu Cys Val Cys Leu Leu Ile Arg Pro Leu
                20                  25                  30

Leu Leu Ser Val Ser Thr Tyr Thr Ser Leu Ile Ile Leu Val Leu Leu
            35                  40                  45

Leu Trp Ile Thr Ala Ala Ser Ala Phe Arg Cys Phe Ile Val Tyr Ile
    50                  55                  60

Ile Phe Val Tyr Ile Pro Leu Phe Leu Ile His Thr His Ala Arg Phe
65                  70                  75                  80

Leu Ile Thr
```